(12) United States Patent
Iannuzzi et al.

(10) Patent No.: US 10,908,067 B2
(45) Date of Patent: Feb. 2, 2021

(54) RAPID NON-DESTRUCTIVE EVALUATION OF THE DEGREE OF SENSITIZATION IN STAINLESS STEELS AND NICKEL BASED ALLOYS

(71) Applicant: VETCO GRAY SCANDINAVIA AS, Sandvika (NO)

(72) Inventors: Mariano Iannuzzi, Nesbru (NO); Atle Helge Qvale, Bekkestua (NO); Alexander Fjeldly, Asker (NO)

(73) Assignee: VETCO GRAY SCANDINAVIA AS, Sandvika (NO)

( * ) Notice: Subject to any disclaimer, the term of this patent is extended or adjusted under 35 U.S.C. 154(b) by 149 days.

(21) Appl. No.: 16/080,035

(22) PCT Filed: Mar. 1, 2017

(86) PCT No.: PCT/EP2017/054742
§ 371 (c)(1),
(2) Date: Aug. 27, 2018

(87) PCT Pub. No.: WO2017/149000
PCT Pub. Date: Sep. 8, 2017

(65) Prior Publication Data
US 2019/0064052 A1    Feb. 28, 2019

(30) Foreign Application Priority Data
Mar. 3, 2016    (NO) .................................... 20160373

(51) Int. Cl.
*G01N 17/02* (2006.01)
*G01N 17/00* (2006.01)
*G01N 33/20* (2019.01)

(52) U.S. Cl.
CPC .......... *G01N 17/02* (2013.01); *G01N 17/006* (2013.01); *G01N 33/20* (2013.01)

(58) Field of Classification Search
None
See application file for complete search history.

(56) References Cited

U.S. PATENT DOCUMENTS 4,066,748 A  *  1/1978  Lietard .................. C01G 49/10
                                                                424/647
4,310,389 A       1/1982  Harbulak
(Continued)

FOREIGN PATENT DOCUMENTS

FR          2676818 A1 *  11/1992  ............... C23G 1/00
JP          S61251762 A      11/1986
(Continued)

OTHER PUBLICATIONS

EPO computer-generated English language translation of Catonne et al. FR 2676818 A1 (Year: 1992).*

(Continued)

*Primary Examiner* — Alexander S Noguerola
(74) *Attorney, Agent, or Firm* — Baker Hughes Patent Organization

(57) ABSTRACT

A method for evaluation of deleterious phase content and distribution in stainless steels and nickel-based alloys based on the correlation between measured open circuit potentials and volume fraction of deleterious phases is disclosed, in conjunction with a portable equipment and apparatus for carrying out the method.

26 Claims, 6 Drawing Sheets

(56) References Cited

U.S. PATENT DOCUMENTS

| | | | |
|---|---|---|---|
| 4,695,360 A | 9/1987 | Asatiani |
| 4,715,218 A | 12/1987 | Sato |
| 2003/0178321 A1 | 9/2003 | Buchler |
| 2008/0179198 A1 | 7/2008 | Burgess |
| 2013/0175030 A1 | 7/2013 | Ige |
| 2014/0246997 A1 | 9/2014 | Suzuki |
| 2016/0160862 A1 | 6/2016 | Torrey |
| 2016/0276970 A1 | 9/2016 | Hawes |

FOREIGN PATENT DOCUMENTS

| | | |
|---|---|---|
| JP | H111316209 A | 11/1999 |
| WO | 0169198 A2 | 9/2001 |
| WO | 2015170991 A1 | 11/2015 |
| WO | 2017087737 A1 | 5/2017 |

OTHER PUBLICATIONS

Daniel Barlow, "Pickling Steel," Feb. 2, 2015, downloaded from the American Galvanizers Association website https://galvanizeit.org/knowledgebase/article/pickling-steel on Apr. 28, 2020 (Year: 2015).*

Luo J S et al; "Identification of the selective corrosion existing at the seam weld of electric resistance-welded pipes," Corrosion Science, vol. 87, pp. 517-520 (Jun. 22, 2014)(Abstract).

Montemor, M.F., et al., "Corrosion behaviour of rebars in fly ash mortar exposed to carbon dioxide and chlorides," Cement and Concrete Composites, vol. 24, Issue. 1, pp. 45-53 (Feb. 1, 2002).

Park, C. J., et al., "Micro-electrochemical polarization study on 25% Cr duplex stainless steel," Materials Science and Engineering, vol. 372, No. 1, pp. 180-185 (2003).

Wilms, M. E., et al., "The effect of sigma-phase precipitation at 800 oC on the corrosion resistance in sea-water of a high alloyed duplex stainless steel," Corrosion Science, vol. 36, No. 5, pp. 871-881 (May 1, 1994).

* cited by examiner

RAPID NON-DESTRUCTIVE EVALUATION OF THE DEGREE OF SENSITIZATION IN STAINLESS STEELS AND NICKEL BASED ALLOYS

FIELD OF THE INVENTION

Embodiments of the present invention relate to an apparatus and a method for evaluation of the degree of sensitization in stainless steels and nickel-based alloys. More precisely, embodiments of the invention provide an apparatus and a method for detecting depletion of passivating elements, in particular due to formation of sigma phase or other deleterious phases in a stainless steel and nickel-based alloys at least containing one or more of the following alloying elements: aluminium (Al), chromium (Cr), cobalt (Co), molybdenum (Mo), nitrogen (N), nickel (Ni), copper (Cu), titanium (Ti) and tungsten (W). Embodiments of the invention also refer to a portable equipment for in situ evaluation of sigma phase content in stainless steel.

BACKGROUND OF THE INVENTION

As used in this application, stainless steel is the common name for iron (Fe) compositions containing carbon (C) and alloying elements that increase the resistance to corrosion. The dominating alloying element in stainless steel is chromium (Cr) which forms a passivating chromium oxide layer on the surface of the steel when the chromium content amounts to at least about 11% by weight (any reference to percentage of fractions made herein refers to percentage by weight if not otherwise stated). Beside chromium, other alloying elements are usually added in order to achieve a desired property, such as resistance to acids, malleability and hardening capacity, e.g. Without excluding any potential alloying element from the general definition of stainless steel as it is used herein, some of the typical alloying elements in stainless steel, beside chromium, are molybdenum (Mo), nitrogen (N), nickel (Ni), copper (Cu) and tungsten (W), which can be added in varying amounts and combinations. Embodiments of the present invention can be applied to iron compositions at least containing one or more of the above mentioned alloying elements.

Further as used in this application, nickel-based alloys refer to solid-solution and precipitation hardened nickel-based alloys and nickel-based super alloys. The nickel (Ni) content typically amounts to about 50% by weight or more in composition with other elements such as chromium (Cr), cobalt (Co), aluminium (Al), titanium (Ti), e.g. Nickel-based alloys provide high temperature strength and oxidation resistance, which makes these alloys useful in parts and components for the oil and gas industry, in pumps, valves, piping and process equipment, in vehicles, spacecraft, ships and submarines, in electric motors, nuclear plants, heat exchangers tubing.

Embodiments of the present invention can further be applied to steel compositions of different crystalline structure including: Martensitic and super martensitic stainless steel (chromium content of about 11-18% and carbon amounting to 0.1-1.2%)

Ferritic and super ferritic (or highly alloyed) stainless steel (chromium content of about 11-30% and carbon below 0.1%)

Austenitic and super austenitic stainless steel (chromium content of about 8-30%, nickel 4-10%, molybdenum 1-8%, and carbon usually below 0.05%)

Ferritic-austenitic stainless steel, also referred to as duplex stainless steel (DSS) and super duplex stainless steel (SDSS) (chromium content 20-25%, nickel content 4-8%, N 0.10-0.30%, Mo 1-4%, W 0-3.5%, Cu 0-3%, and carbon below 0.03%)

Precipitation hardening stainless steels: these steels can be matrensitic, austenitic, or a combination. These steels can be hardened by heat treatment.

Among the stainless steels, the DSS and SDSS steel grades are of special importance in engineering and construction given their good combination of strength and corrosion resistance. The two-phase ferritic-austenitic micro structure composition with a ferrite to austenite ratio of about 35-55% in the DSS or SDSS steel qualities combines high strength with good workability and welding properties. Together with the ability to resist corrosion in a variety of aggresive environments these engineering qualities make the DSS and SDSS steels suitable for employment in, for example, seawater applications and in subsea engineering structures. vehicles at land and sea, air and space craft, power plants, process industry and in chemical applications.

Stainless steel, and in particular DSS and SDSS are, however, susceptible to the precipitation of deleterious phases when subjected to a critical temperature for a certain amount of time, such as the temperatures reached during welding. Precipitation of intermetallic phases that are not the matrix or the alloy as it is normally used affect both mechanical properties and corrosion resistance. A high content of chromium and molybdenum can promote the precipitation of intermetallic phases such as sigma phase, chi and chromium nitrides ($Cr_2N$) when subjected to temperatures in the range of 300-900° C. Among the deleterious phases, sigma phase is considered the most detrimental. Sigma phase is an intermetallic compound rich in chromium and molybdenum with a volume fraction that is larger than that of any other precipitated intermetallic phase. Precipitation of sigma phase depleates chromium and molybdenum from the surrounding ferritic-austenitic matrix, causing locally a weakening of the corrosion resistance ultimately leading to pitting or crevice corrosion.

Since the phase transformation kinetics of sigma phase is relatively fast, taking less than 1.8 minutes at 870° C. for the onset of sigma phase precipitation, the content and volume fraction of sigma phase precipitates can serve as an indicator of the status of the corrosion resistance of a stainless steel structure.

However, evaluation of sigma phase content in a stainless steel sample using known and standardized methods requires that the microstructure is exposed by sectioning, polishing or etching, such as required in following the international standards ASTM A923 and ASTM E562 which include 24 h corrosion tests, impact toughness measurements, and systematic manual point counting procedures for statistically estimating the volume fraction of an identifiable constituent or phase from sections through the microstructure using a microscope and a point grid.

SUMMARY OF THE INVENTION

An object of embodiments of the present invention is to provide a method and apparatus for non-destructive evaluation of the status of corrosion resistance in stainless steels and nickel-based alloys.

The object is met in the method and apparatus for detecting depletion of passivating elements, in particular due to the formation of sigma phase or other deleterious phases, in accordance with the accompanying claims.

The method and apparatus of embodiments of the present invention can be applied to stainless steel and nickel-based alloys at least containing one or more of the following alloying elements: aluminium (Al), chromium (Cr), cobalt (Co), nickel (Ni), molybdenum (Mo), nitrogen (N), copper (Cu), titanium (Ti) and tungsten (W).

The method and apparatus of embodiments of the present invention can be applied in a quality control procedure performed at any stage from the production of a steel ingot to the inspection of a structure or component before or after being put into operation.

Embodiments of the present invention provide an additional advantage by the fact that it can be applied in situ for detection of deleterious phases in the field.

In an embodiment of the present invention an apparatus is provided, the apparatus comprising:
- a container containing a liquid or a gelatinized electrolyte,
- a specimen interface on the container providing contact between the electrolyte and the surface of a test specimen,
- a reference electrode in the container in electrochemical contact with the test specimen via the electrolyte, and
- a voltmeter electrically connected between the reference electrode and the test specimen.

In another embodiment of the present invention a method is provided, the method comprising:
i) providing a container containing a liquid or a gelatinized electrolyte,
ii) providing a reference electrode in electrochemical contact with a test specimen via the liquid or gelatinized electrolyte,
iii) electrically connecting the reference electrode with the test specimen over a voltmeter,
iv) reading and recording open circuit potential (Eoc) values in bulk or at each testing point of the specimen,
v) comparing the Eoc values of the test specimen with the open circuit potential of a sigma phase free sample (negative control specimen) of the steel of the test specimen.

Comparative tests have shown that the method and the apparatus of embodiments of the present invention will unambigously detect the presence of deleterious phases, in particular the presence of sigma phase which causes severe depletion of passivating elements from solid solution, leading to a sensitized microstructure and low pitting potential at the matrix/particle interface. When a sensitized microstructure is subjected to an acidic and oxidizing environment localized corrosion will initiate at areas with the lowest pitting potential. The open circuit potential Eoc is, then, controlled by the pitting potential of the Cr—Mo depleted region. Below the critical pitting temperature the Eoc of a solution annealed sample free of sigma phase is typically very high—mean value approximately 0.7 V vs. the saturated calomel electrode (SCE) used as reference in the tests. However, the presence of a sigma phase content as low as 0.5% by volume decreases Eoc dramatically—mean value approximately 0.4 V vs. the SCE reference electrode. The drop in Eoc is a function of the sigma phase content and it is virtually instantaneous. Thus, the range of open circuit potentials Eoc can be used as a fast and accurate indicator for determining the degree of sensitization in a sample of stainless steel.

The temperature of the test solution can vary between 20 to 85° C. depending on the type of stainless steel in question.

The correlation between open circuit potential Eoc and, e.g., sigma phase content has been confirmed in cyclic potentiodynamic polarization tests in NaCl solutions and long term Eoc exposure using 6% $FeCl_3$ (pH 1.10) as electrolyte. The test results are demonstrated in the accompanying diagrammatic drawings.

In the drawings, FIG. 1 illustrates the change in Eoc in effect of a growing content of sigma phase precipitates in a 25Cr super duplex stainless steel test specimen. FIG. 2 illustrates the difference in Eoc over time in a 0.5 vol. % sigma phase test specimen relative to the measured Eoc of a sigma phase free (solution annealed) control specimen. The steel used in the tests was of FIGS. 1 and 2 UNS S32750 which is a ferritic-austenitic SDSS grade steel often used, among other components, in subsea pipelines, forged and hot isostatically pressed connectors, as well as small bore tubing and bolting. The test temperature of this example was 50° C.

Statistical analysis performed on the same steel shows that the sigma phase free and the 0.5 vol. % sigma phase containing samples display non-overlapping density functions that define two distinctly separated distribution areas, see FIG. 3. The distinctive distributions of Eoc provide further empirical basis for relying on the correlation between open circuit potential Eoc and sigma phase content in the method and apparatus of embodiments of the present invention.

Embodiments of the apparatus comprise a number of features which can be applied separately or in different combinations. Among the features which characterize embodiments of the apparatus are, briefly stated:

An electrolyte including an acidic chloride solution, more particularly, ferric chloride ($FeCl_3$) or any other oxidising agent of similar polarization capacity.

A container wherein the specimen interface is arranged in a lower end.

A tubular container wherein the container diameter is dimensioned to retain the electrolyte within the tubular container through capillary action.

A tubular container being a micro-capillary tube having an inner diameter in the range of 0.05-5.0 mm, more particularly, in the range of 0.05-0.5 mm.

A specimen interface comprising a perforated or porous membrane in the lower end of the container.

A positioning means in the form of a circumferential sleeve extending beyond the lower end of the container, a lower end of the sleeve providing a base for standing the container on the surface of a test specimen.

A perforated or porous membrane arranged inside a surplus length portion of the sleeve of the positioning means.

A positioning means with a standing base carrying a glue or an adhesive on its lower side that permits temporary attachment to the test specimen.

A reference electrode in the form of a wire extended into the container/tube from a sealed upper end of the container/tube.

A reference electrode in the form of a silver wire coated with silver chloride (Ag/AgCl electrode) or a pure tungsten (W) wire.

A set of containers with reference electrodes individually connected to separate inputs of a multichannel voltmeter via a terminal block and a coupling interface.

A positioning means arranged as holder for the reference electrodes and more particularly, also for the terminal block and coupling interface.

A resistive heating element and a thermocouple may be installed in order to vary and control the temperature of the electrolyte.

In analogy herewith embodiments of the present invention also relate to a portable equipment for in situ evaluation of deleterious phase content in stainless steels or nickel-based alloys comprising an apparatus according to any previous embodiment, wherein the reference electrode is associated with a positioning means for temporary locating the reference electrode in a measuring point on a test specimen.

An alternative embodiment of the portable equipment comprises a positioning means arranged for accommodation of a number of reference electrodes for the simultaneous positioning of an array of reference electrodes on the test specimen.

The portable equipment may further comprise a processing unit, a display and a printer or plotter.

Embodiments of the method comprises a number of steps which can be applied separately or in different combinations. Among the steps which characterize embodiments of the method are, briefly stated:

the step of repeating step iv) until the whole test specimen or the area of interest is examined, and generating, based on the sum of readings, an estimate of the amount of deleterious phase content in the test specimen using a calibration curve mapping the correlation between Eoc and deleterious phase content in the material of the test specimen;

the step of preparing, for the alloy of the test specimen, a calibration curve covering EOC vs. deleterious phase content down to a deleterious phase content of 0.5% by volume, or less;

the step of providing a capillary or a micro-capillary tube containing the reference electrode submerged in the electrolyte, and scanning the test specimen for mapping of deleterious phase content at a spatial resolution in the range of 0.05 to 5.0 mm, more particularly, in the range of 0.5-0.05 mm;

the step of preparing an electrolyte gel containing ferric chloride ($FeCl_3$) at 1 to 6% by weight;

the alternative step of preparing an electrolyte gel containing other acidic and oxidizing chloride solution that produces a potential equal to or above that of ferric chloride ($FeCl_3$);

the step of providing the reference electrode in the form of an Ag/AgCl wire electrode or a pure tungsten (W) electrode or any other suitable reference electrode;

the step of forming an array of reference electrodes, and reading and recording a matrix of Eoc values through a multichannel voltmeter;

the step of applying the method in a quality control procedure;

the step of applying the method in situ for sigma phase detection in the field.

BRIEF DESCRIPTION OF THE DRAWINGS

Embodiments of the method and apparatus of the present invention will be further explained in the following with reference made to the accompanying schematic drawings. In the drawings

DETAILED DESCRIPTION

Figure 1:
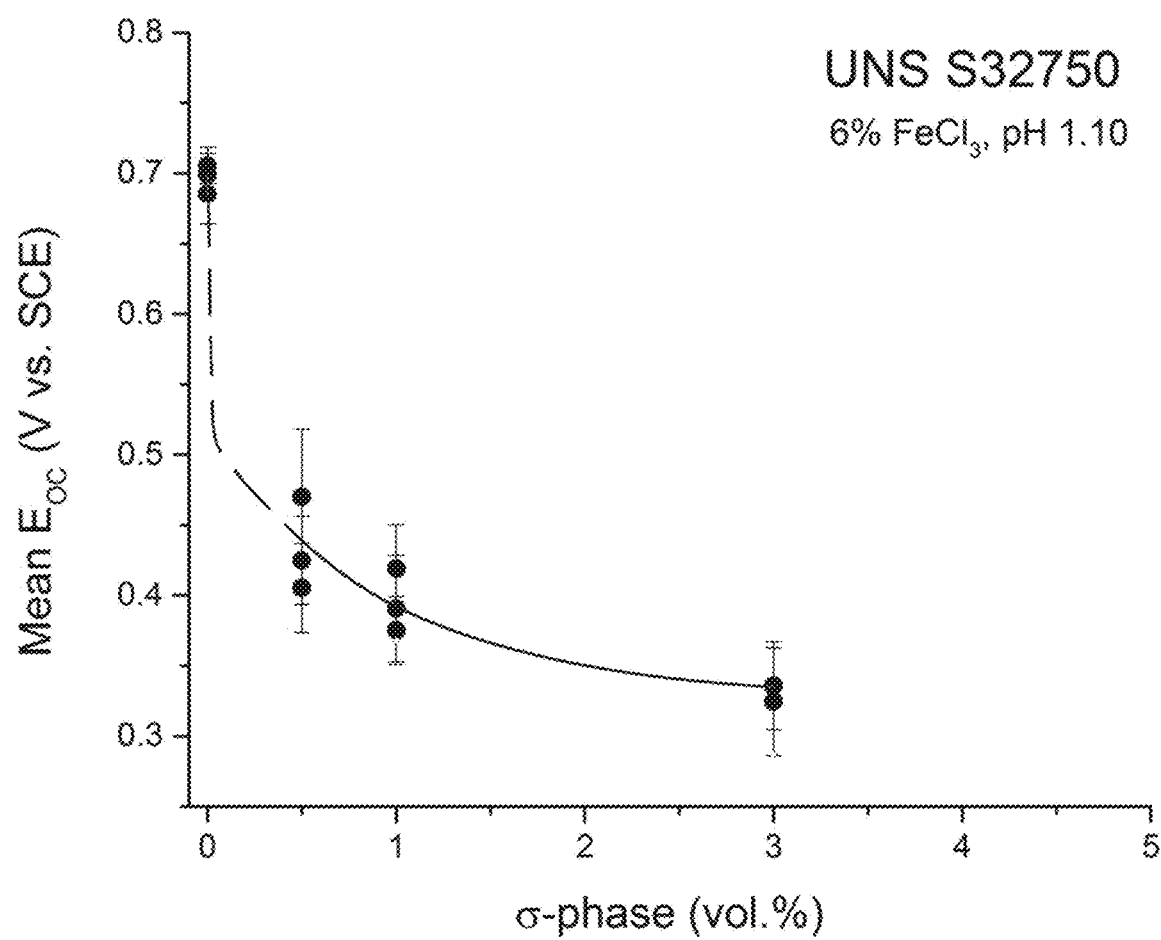
FIG. 1 is a diagram showing the correlation between Eoc and the fractional amount of sigma phase precipitates in a test specimen.
Figure 2:
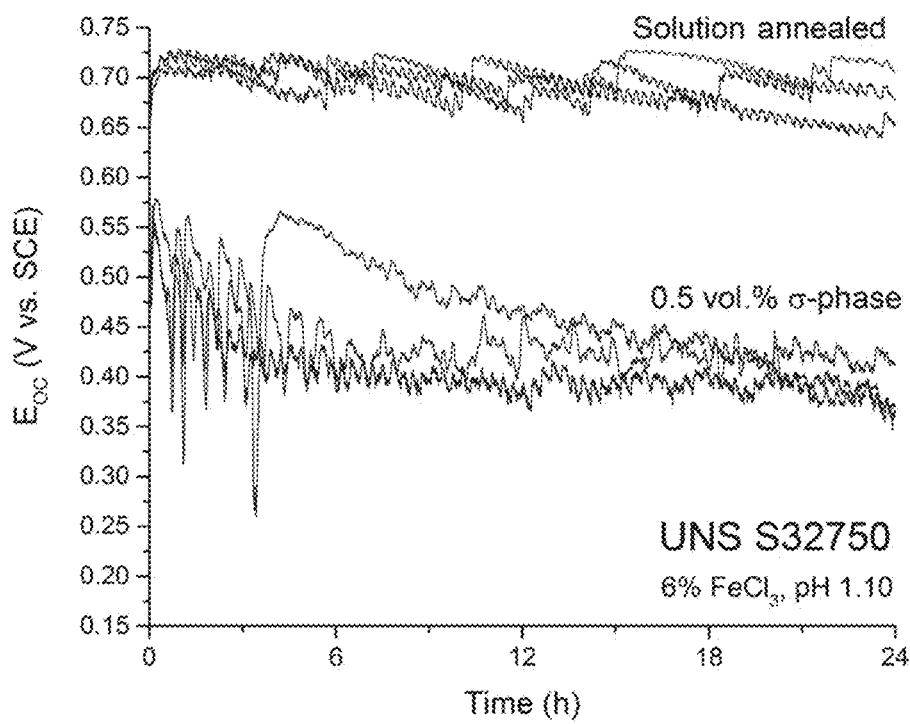
FIG. 2 is a diagram showing the difference in Eoc over time in a 0.5 vol. % sigma phase 25Cr super duplex stainless steel specimen relative to the measured Eoc of a sigma phase free (solution annealed) control specimen.
Figure 3:
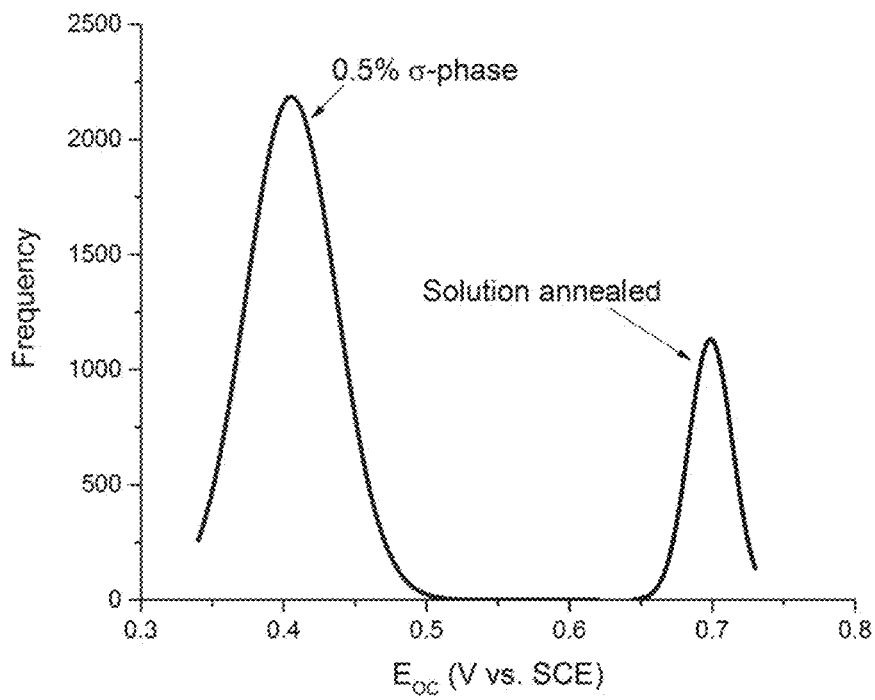
FIG. 3 is a diagram displaying non-overlapping distribution areas in statistical analysis of Eoc of the sigma phase-free and the 0.5 vol. % sigma phase containing samples of FIG. 2.

FIGS. 1-3 have been discussed hereinabove under the subtitle Summary of embodiments of the invention.

In addition to what is already discussed with reference to FIG. 1 it shall be further noted that the functional correlation between Eoc values and fractions of sigma phase precipitates as confirmed and shown by the plotted diagram of FIG. 1 is used in embodiments of the invention for calibration of the test equipment and method. For the UNS 532750 steel, the curve connecting the plotted Eoc values in FIG. 1 demonstrates the functional correlation between sigma phase concentration and open circuit potential Eoc down to a sigma phase concentration of 0.5% by volume (the curve portion connecting the Eoc values of 0.5 vol. % sigma phase with the values of the sigma phase free sample is an estimate).

In a corresponding way calibration curves can be established for other stainless steel families as well as for other corrosion resistant alloys, and used for reading out sigma phase or other deleterious phase concentrations based on measured Eoc values.

In this connection, it should be emphasized that embodiments of the invention can be applied for detection and evaluation of other deleterious phases than sigma phase, such as chromium nitride and carbides etc., all of which deplete Cr and Mo from solid solution and lower the pitting potential of the affected area in the microstructure. The localized Cr and Mo depletion, in turn, lowers the open circuit potential of the test specimen.

Figure 4:
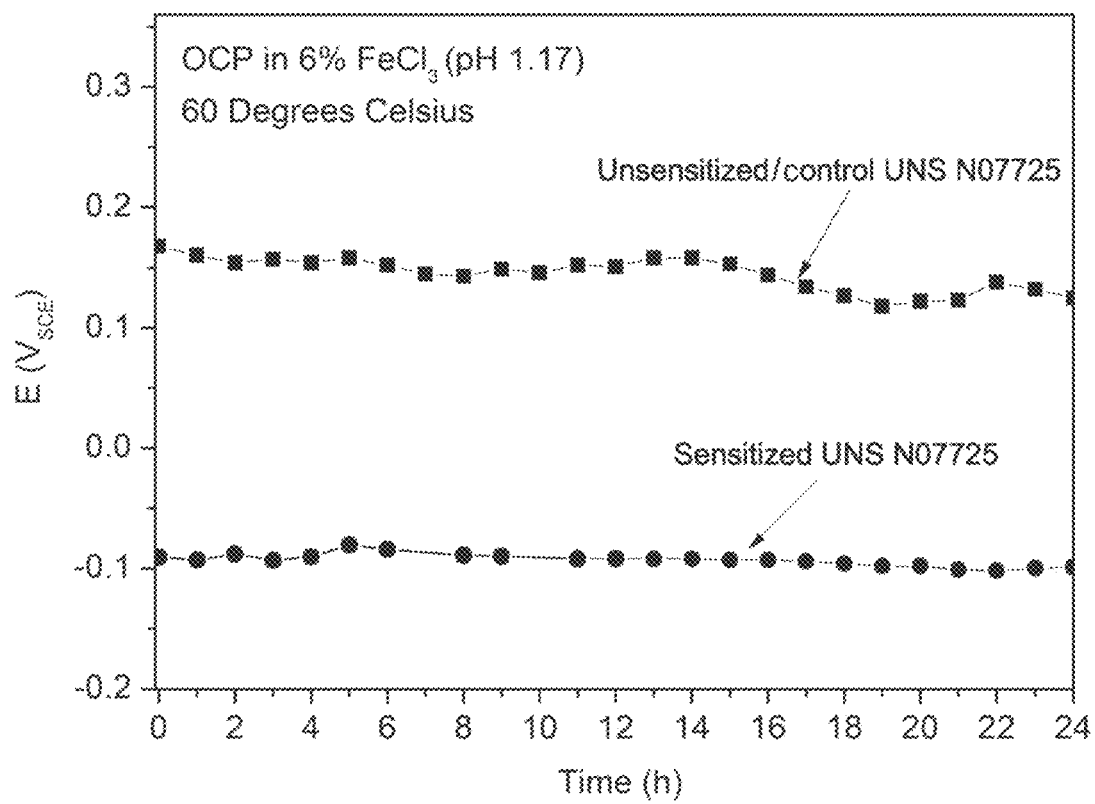
FIG. 4 is a diagram showing the difference in Eoc over time in a sensitized nickel-based alloy specimen relative to the measured Eoc of a control specimen.

In precipitation hardening nickel-based alloys, precipitation of deleterious phases such as nanometre-sized sigma phase at grain boundaries, leads to a similar drop in open circuit potential as demonstrated above for stainless steel. FIG. 4 illustrates the development of Eoc over time in a sensitized test specimen relative to the measured Eoc of a control specimen free of deleterious phases. The test illustrated in FIG. 4 was performed on nickel-based alloy UNS NO7725 which is a precipitation hardened material of extreme high strength, i.e. 120 Ksi yield strength, containing 50.0-59.0% wt. nickel, 19-22.5% Cr, 7.0-9.5% Mo, 2.75-4.0% Nb, and 1.0-1.7% Ti.

Figure 5:
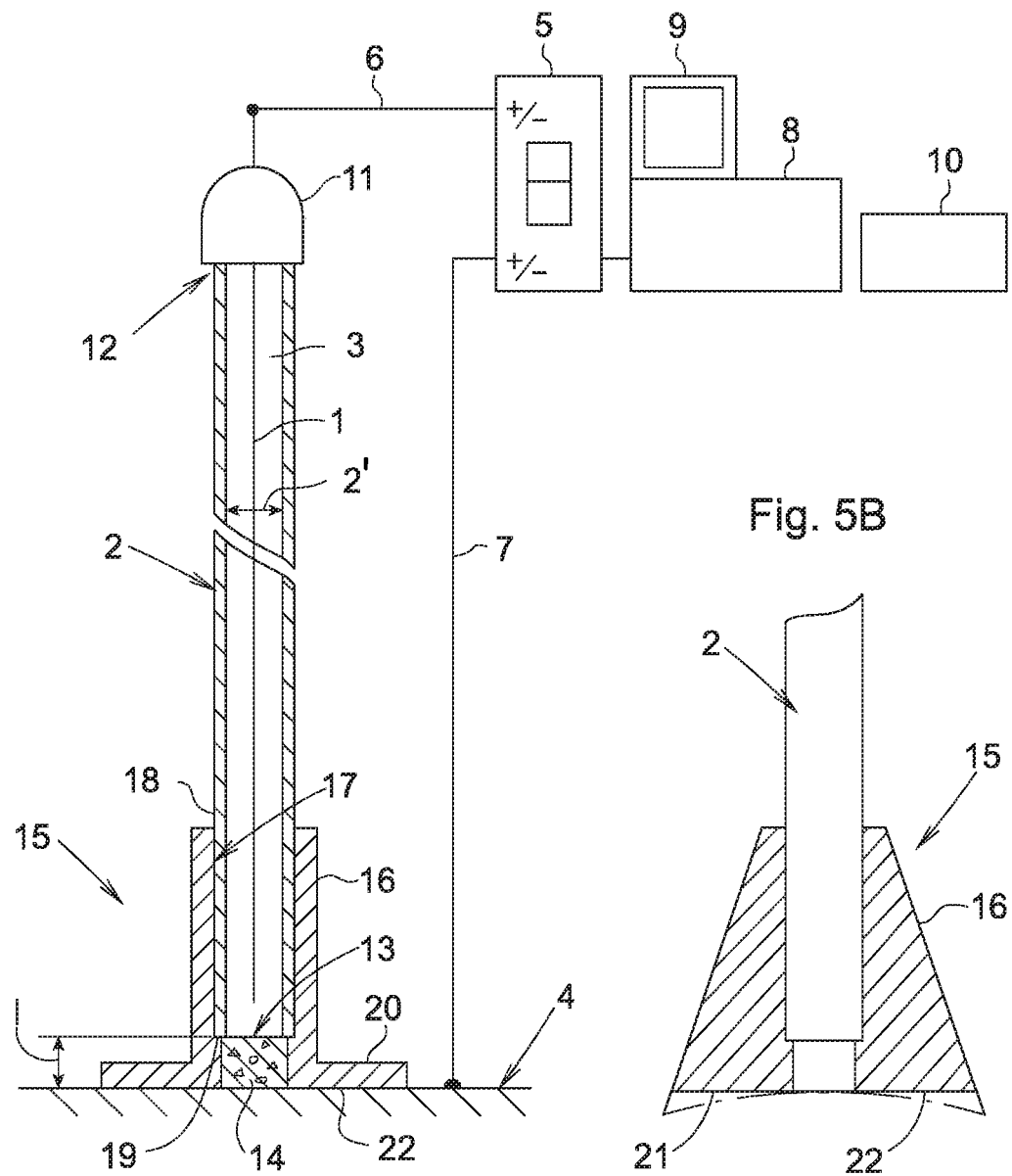
FIG. 5A illustrates schematically the configuration of an apparatus designed for carrying out the method of embodiments of the present invention.
FIG. 5B is a partial view showing an alternative embodiment of a positioning means employed in the apparatus of embodiments of the present invention.

With reference to FIG. 5A an apparatus for exercising the method of embodiments of the present invention comprises a reference electrode 1 which is inserted in a container 2 containing an electrolyte 3. The electrolyte 3 comprises a liquid or gelatinized oxidising agent by which the reference electrode 1 can be put in electrochemical contact with a test specimen 4. A voltmeter 5 is electrically connected between the test specimen and the reference electrode via conductors 6 and 7. It should be noted that for ease of reading and understanding the representation of FIG. 5A is not true to scale.

The voltmeter 5 can be an off-the-shelf instrument known as a potentiostat or galvanostat by which the potentials of the reference electrode and test specimen can be frequentially monitored and varied by application of a current through the electrolyte in a polarization scanning procedure as is known per se. The voltmeter is associated with a data processing unit 8 via a data bus. The data processing unit 8 is operational for receiving, processing, storing and displaying data recorded by the voltmeter. The voltmeter 5 and processing unit 8 form parts of a network, by wire or wireless, including at least a display 9 and a printer or plotter 10 by which the results of the scanning procedure can be presented in the form of plots, tables, data maps etc., as desired. Some or all of the operational units such as the voltmeter, the processor, the display and the printer/plotter can be integrated in a portable equipment if convenient. Software and mobile applications can interface with the device as well as record and report the results.

The containerized electrolyte 3 is prepared from an acidic and oxidizing chloride solution, more particularly, including ferric chloride, $FeCl_3$, at a concentration of 1-6% by volume and a pH value of about 1.0 to 1.20. Other oxidising agents may alternatively be used as the electrolyte in container 2, more particularly, any other oxidising agent which will polarize the test specimen to a potential similar to that of 1-6 wt. % $FeCl_3$.

In an embodiment the reference electrode 1 is a miniaturized silver/silver chloride (Ag/AgCl) electrode or a pure tunsgten wire. Other electrodes with a stable and well-known electrode potential relative to the standard hydrogen electrode may be used as reference electrode in the apparatus of embodiments of the invention. The reference electrode 1 is prepared from a silver wire coated with silver chloride and inserted in the electrolyte 1 in a tubular glass or plastic container 2 of capillary or micro-capillary dimensions. In this context, the expressions capillary and micro-capillary refer to a tube with an inner diameter 2' capable of retaining the electrolyte in the tube through capillary action. Depending on the viscosity of the liquid or gelatinized electrolyte the inner diameter 2' of a tubular container 1 may be in the range of about 0.05-5.0 mm, more particularly, in the range of 0.05-0.5 mm. For electric connection with external equipment the reference electrode is extended through a cap 11 which seals a first and upper end 12 of the container.

The container 2 has an open second and lower end forming a specimen interface 13 in the mouth of the container, through which the electrolyte with oxidising agent comes to contact with the surface of the test specimen. A perforated or porous membrane 14 covers the specimen interface in said lower end. The membrane 14 may be realized as a sintered ceramic, glass or silica element, e.g.

A key feature of embodiments of the present invention is the mobility of the apparatus for evaluation of sigma phase content and other deleterious phases in stainless steel and nickel-based alloys, thus mapping the status of corrosion resistance in the material. The mobility makes the apparatus equally suitable for quality control procedures on bulk material as for evaluation of deleterious phase content in material and welded structures in the field.

For the purpose of temporary positioning and optionally attaching the container 2 onto the test specimen during a polarization test, the container is equipped with a positioning means 15. Similar to the container 2, the positioning means 15 can be made of glass or plastic material insensitive to the acidic electrolyte 3. In the embodiment of FIG. 5A the positioning means 15 comprises a sleeve 16 with a circumferential wall and an inner periphery 17 that mates with the outer periphery 18 of the container. In the mounted position on the container, the sleeve extends beyond the lower end of the container for a length 1 of a few mm, such as from about 5-15 mm. A radial shoulder 19 may be formed on the inner periphery of the sleeve to define the length of insertion of the container into the sleeve. The surplus length 1 of the sleeve may serve as a seat for fixation of the porous membrane 14.

The sleeve 16 may be shaped as a straight cylinder, in its lower end connected to a flange 20 that extends radially outside the sleeve as illustrated in FIG. 5A. An alternative sleeve may have a conical wall, the larger radius of which forms a bottom end face 21 of the sleeve as illustrated in FIG. 5B. In both cases the positioning means 15 forms a standing base that provides added stability to the container when positioned on the test specimen.

The flange 20 and the bottom end face 21 each provides a base which can be formed planar for positioning the container on planar test surfaces as illustrated. This base can alternatively be curved for positioning the container on pipes, rods or other non-planar surfaces as shown in dash-dot lines in FIG. 5B.

A repositionable glue or adhesive 22 may, in an embodiment, be applied to the base of the positioning means for detachably attaching the positioning means and container with the reference electrode to the test specimen.

Albeit being disclosed as a separate element for mounting on the container 2, it will be understood that the positioning means 15 may optionally be realized as a structural part that is formed integrally with the container.

A heating element such as heat resistance wire e.g., may be wrapped about the container or inserted in the electrolyte in order to vary the temperature of the electrolyte if appropriate. A thermocouple may be arranged to control the temperature.

Figure 6:
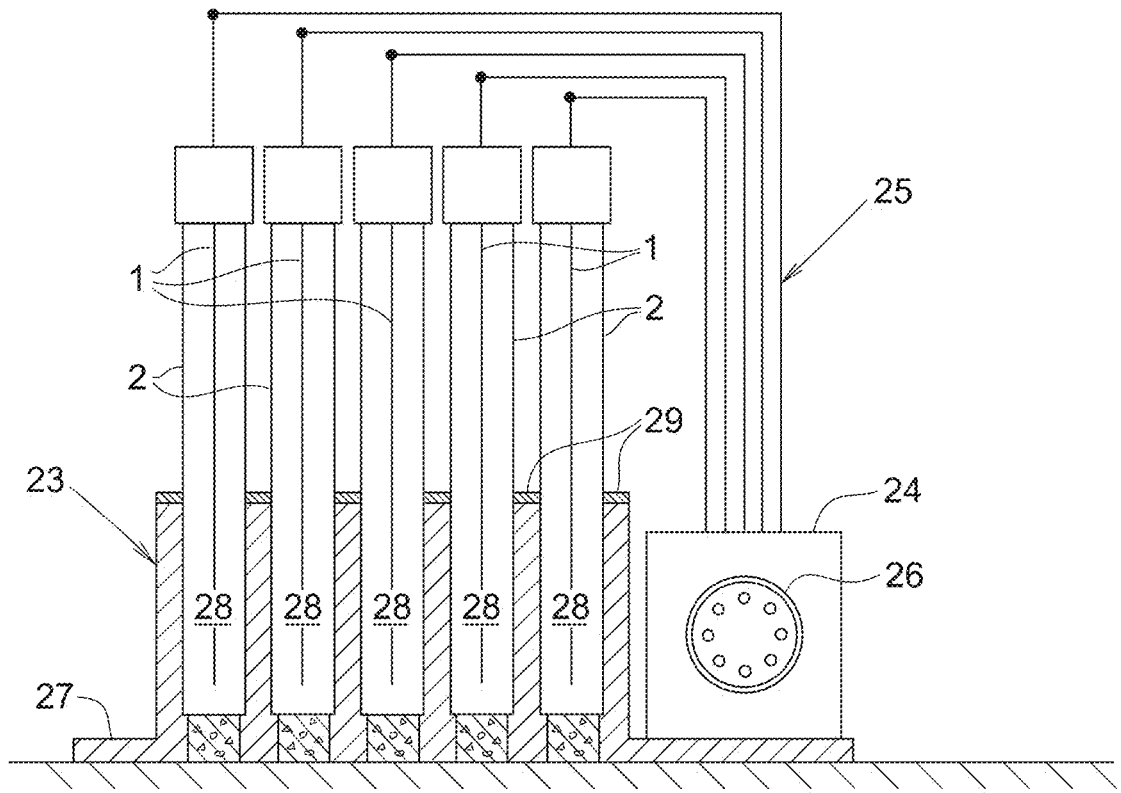
FIG. 6 is a schematic illustration of an alternative configuration of the apparatus.

An alternative embodiment of the apparatus is schematically shown in FIG. 6. It should be noted that for ease of reading and understanding the representation of FIG. 6 is not true to scale. In the embodiment of FIG. 6 the reference electrode 1 is multiplied in a set of sensors, each sensor comprising a reference electrode in a container containing a liquid or gelatinized electrolyte. The reference electrodes 1 are individually connected to a multichannel voltmeter with a corresponding number of input terminals (voltmeter not shown).

The containers 2 and electrodes 1 are supported in a positioning means arranged as a holder 23 carrying a terminal block 24 that collects the electrode wires 25 and provides a coupling interface 26 towards the voltmeter. Feet 27 in the lower side of the holder 23 form a standing base that provides stability to the set of sensors when supported on the surface of a specimen during testing. In order to ensure electrolytic contact between the test specimen and each reference electrode, the containers are adjustable and movable in relation to the holder in the length direction of the containers. To this purpose the holder 23 is formed with a respective guiding slot 28 that provides a seat for accommodation of a container. Slide bearings 29 may be arranged in connection with the slots 28 in order to arrest the containers in mounted position through frictional engagement.

The holder 23 may be sized to provide an array of sensors/reference electrodes arranged in one row or in several parallel rows permitting simultaneous reading and recording of a matrix of Eoc values. Sensor arrays of other configurations than rectangular are of course possible.

The voltmeter records the Eoc vs time for a given time interval until a stable reading is obtained. By successively moving the apparatus over the area to be examined the degree of sensitization and distribution of sensitized areas of the test specimen can be mapped with a resolution determined by the diameter dimensions of the container and standing base of the positioning means, or by the diameter of the container and the interspace between adjacent containers in the sensor array. With regards to the sizes of micro-capillary tubes available for the purpose, embodiments of the invention comprise mapping of deleterious phase content at spatial resolutions in the range of 0.05 to 5.0 mm, more particularly, in the range of 0.5-0.05 mm.

Figure 7:
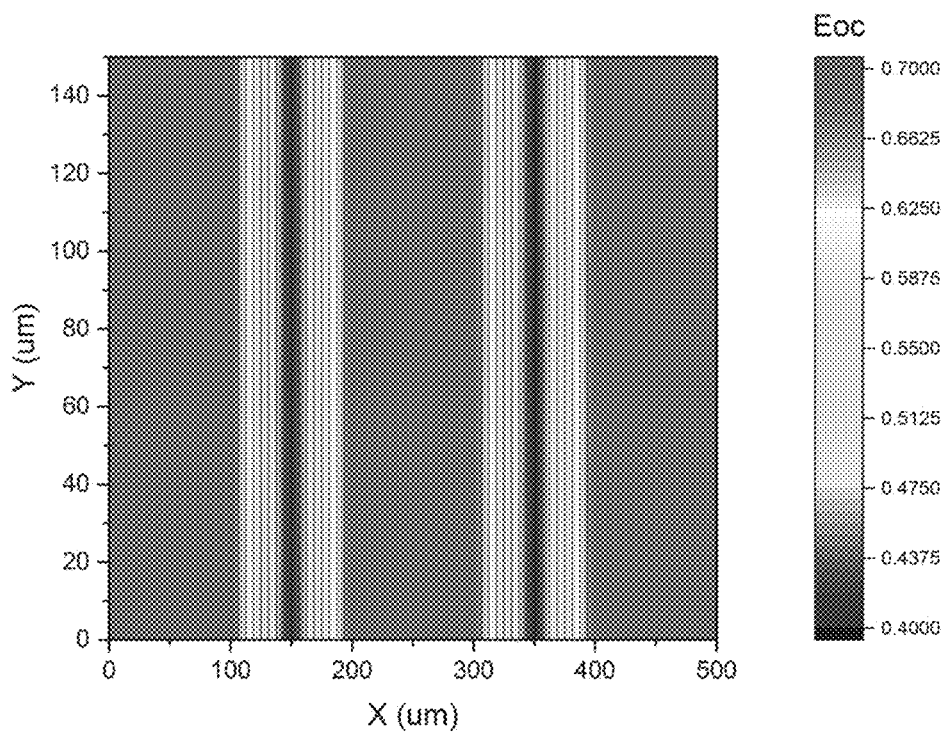
FIG. 7 is a 2-dimensional plot illustrating the area distribution of sigma phase precipitates in a test specimen.
Figure 8:
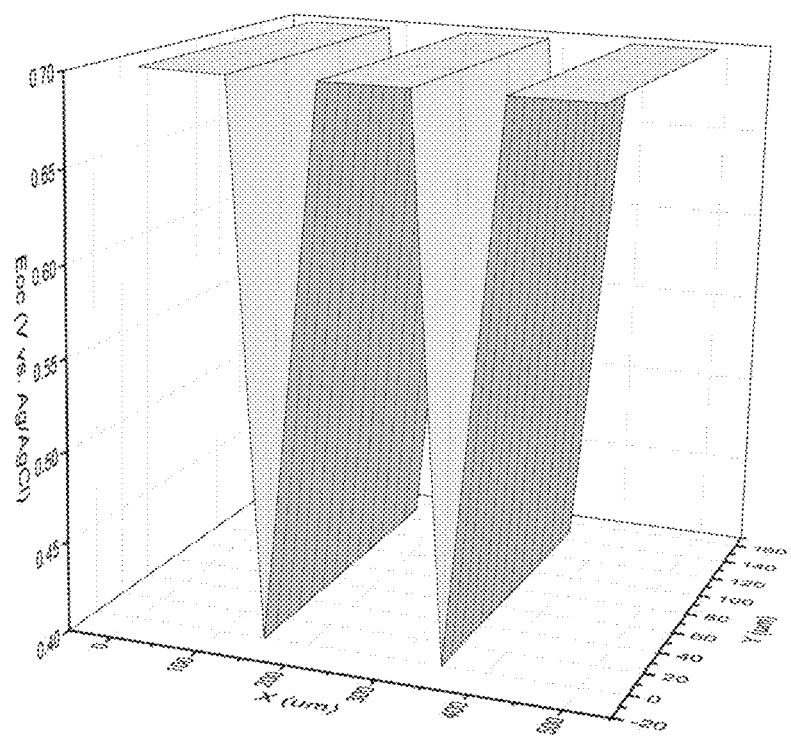
FIG. 8 is a 3-dimensional plot illustrating the spatial distribution of sigma phase precipitates in a test specimen.

For visual representation of the test result, the collected data can be presented in 2- or 3-dimensional plots. FIG. 7 is one example of a 2-dimensional plot illustrating the area distribution and concentration of sigma phase precipitates in a test specimen based on the range of recorded Eoc values. FIG. 8 is an example of a 3-dimensional plot illustrating the spatial distribution and concentration of sigma phase precipitates in a test specimen based on the range of Eoc values as recorded through the method and apparatus of embodiments of the present invention.

Embodiments of the invention are illustrated and described provides the advantage of rapid and non-destructive testing of stainless steel and nickel-based alloys for detecting the occurrence of deleterious phases and for evaluation of the status of the corrosion resistance. Although the major benefits reside in the mobile application it should be noted that in alternative use a test sample may be exposed to the electrolyte in a quality control evaluation using test specimens in a destructive way. The listing below includes a majority of the corrosion resistant alloys to which embodiments of the present invention can be applied:

1) Austenitic and super (also known as highly alloyed) austenitic stainless steels
UNS S31600 and S31603
UNS S30400 and S30403
UNS S31700
UNS S34500
UNS S32100
UNS S20910
Type 6Mo Stainless Steel (e.g. UNS S39254, J93254, N08367, N08925)
Type 7Mo UNS S32654
N08926
J95370

2) Duplex and super duplex stainless steels
Type 22Cr duplex stainless steels (UNS S31803, S32550)
Type 25Cr DSS or SDSS (UNS S32750, S32760, S39274, S39277)
Lean DSS (UNS S32101, S32304)

3) Ferritic and super (or highly alloyed ferritic) stainless steels
UNS S44400
UNS S43000
UNS S40900
UNS S40500
UNS S44700

4) Martensitic and super martensitic stainless steels
UNS S41000
UNS S41425
UNS S41426
UNS S41500
UNS S42500
UNS J91540
SM17CRS-12

5) Precipitation hardened stainless steels
UNS S66286
UNS S15500
UNS S17400
UNS S45000
UNS S15700

6) Solid-solution nickel based alloys
UNS N06625
UNS N06022
UNS N06059
UNS N06686
UNS N07022
UNS N08026
UNS N10276
CW12MW 7) Precipitation hardenable nickel based alloys
UNS N07718
UNS N07725
UNS N07716
UNS N09925
UNS N09945
UNS N06625
UNS N07626

Although it will be realized that in alternative use a test sample may be exposed to the electrolyte in a quality control using test specimens in a destructive way, the major benefits provided by embodiments of the the present invention reside in the mobile and non-destructive implementation.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An apparatus for detecting depletion of passivating elements due to formation of sigma phase and/or other deleterious phases, in stainless steels or nickel-based alloys at least containing one or more of the following alloying elements:
   aluminium, chromium, cobalt, nickel, molybdenum, nitrogen, copper, titanium and tungsten, the apparatus comprising:
   a tubular container containing a liquid or a gelatinized electrolyte;
   a specimen interface arranged in a lower end of the tubular container to provide contact between the electrolyte and a surface of a test specimen;
   a reference electrode in the tubular container in electrochemical contact with the test specimen via the electrolyte; and
   a voltmeter electrically connected between the reference electrode and the test specimen.

2. The apparatus of claim 1, wherein the electrolyte is an acidic chloride solution.

3. The apparatus of claim 2, wherein the electrolyte is ferric chloride.

4. The apparatus of claim 1, wherein the tubular container diameter is dimensioned to retain the electrolyte within the container through capillary action.

5. The apparatus of claim 1, wherein the tubular container is a micro-capillary tube having an inner diameter in the range of 0.05-5.0 mm.

6. The apparatus of claim 1, wherein the specimen interface comprises a perforated or porous membrane covering the specimen interface in the lower end of the tubular container.

7. The apparatus of claim 6, wherein the perforated or porous membrane is arranged inside the sleeve.

8. The apparatus of claim 1, further comprising a circumferential sleeve extending beyond the lower end of the tubular container, a lower end of the circumferential sleeve providing a base to enable the tubular container to stand on the surface of the test specimen.

9. The apparatus of claim 8, wherein the base carries a glue or an adhesive that permits temporary attachment of the tubular container to the test specimen.

10. The apparatus of claim 1, wherein the reference electrode is a wire extended into the tube from an upper end of the tube.

11. The apparatus of claim 10, wherein the reference electrode is a silver wire coated with silver chloride, a pure tungsten wire, or any other reference electrode capable of providing a stable reading.

12. The apparatus of claim 1, comprising a set of reference electrodes separately connectable to individual inputs of a multichannel voltmeter via a terminal block and a coupling interface.

13. A portable equipment for in situ evaluation of deleterious phase content in stainless steels and nickel-based alloys comprising an apparatus according to claim 1, wherein the reference electrode is associated with a base to temporarily locate the reference electrode at a measuring point on a test specimen.

14. The portable equipment of claim 13, wherein the base is configured to accommodate a number of reference electrodes to simultaneously position an array of reference electrodes on the test specimen.

15. The portable equipment of claim 13, further comprising a processing unit, a display and a printer or plotter.

16. An apparatus for detecting depletion of passivating elements due to formation of sigma phase and/or other deleterious phases, in stainless steels or nickel-based alloys at least containing one or more of the following alloying elements: aluminium, chromium, cobalt, nickel, molybdenum, nitrogen, copper, titanium and tungsten, the apparatus comprising:
containers, each of the containers containing a respective liquid or a gelatinized electrolyte;
specimen interfaces, each of the specimen interfaces arranged in a lower end of a respective one of the containers to provide contact between the electrolyte in each of the containers and a surface of a test specimen;
a set of reference electrodes, each of the electrodes arranged in a respective one of the containers and in electrochemical contact with the test specimen via the electrolyte in the respective one of the containers;
a multichannel voltmeter electrically connected between the set of reference electrodes and the test specimen, wherein each electrode of the set of reference electrodes is separately connectable to individual inputs of the multichannel voltmeter via a terminal block and a coupling interface; and
a holder for positioning the set of reference electrodes, the terminal block and the coupling interface.

17. A method for detecting depletion of passivating elements in particular due to formation of sigma phase or other deleterious phases, in stainless steels or nickel-based alloys at least containing one or more of the following alloying elements: aluminium, chromium, Cobalt, nickel, molybdenum, nitrogen, copper, titanium and tungsten, the method comprising:
placing a reference electrode in a container containing a liquid or a gelatinized electrolyte such that the reference electrode is in electrochemical contact with a test specimen via a specimen interface arranged in a lower end of the container;
electrically connecting a voltmeter between the reference electrode and the test specimen;
reading and recording open circuit potential values at each testing point of the test specimen; and
comparing the open circuit potential values with an open circuit potential of a sigma phase free sample of steel of the test specimen.

18. The method of claim 17, further comprising:
repeating comparing until the whole test specimen or an area of interest is examined; and
generating, based on the sum of readings, an estimate of an amount of deleterious phase content in the test specimen using a calibration curve mapping a correlation between open circuit potential and sigma phase content in the steel of the test specimen.

19. The method of claim 18, further comprising:
preparing, for the material of the test specimen, a calibration curve covering open circuit potential vs. deleterious phase content down to a deleterious phase content of 0.5% by volume or less.

20. The method of claim 17, further comprising:
providing the container in form of a micro-capillary tube containing the reference electrode submerged in the liquid or gelatinized electrolyte; and
scanning the test specimen for mapping of deleterious phase content at a spatial resolution in the range of 0.05 to 5.0 mm.

21. The method of claim 17, further comprising:
preparing an electrolyte gel containing ferric chloride at 1 to 6% by weight.

22. The method of claim 17, further comprising:
preparing an electrolyte gel containing an acidic and oxidizing chloride solution that produces a potential equal to or above that of ferric chloride.

23. The method of claim 17, further comprising:
providing the reference electrode in the form of an Ag/AgCl wire electrode or a pure tungsten wire.

24. The method of claim 17, further comprising:
forming an array of reference electrodes; and
reading and recording a matrix of open circuit potential values through a multichannel voltmeter.

25. The method of claim 17, comprising applying the method in a quality control procedure where test specimens can be exposed to the electrolyte in bulk.

26. The method of claim 17, comprising applying the method in situ for deleterious phase detection in the field.

* * * * *